US006897661B2

(12) United States Patent
Allen et al.

(10) Patent No.: US 6,897,661 B2
(45) Date of Patent: May 24, 2005

(54) METHOD AND APPARATUS FOR DETECTION OF CONTAMINANTS IN A FLUID

(75) Inventors: David Allen, Willoughby, OH (US); Michael A. Centanni, Parma, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 10/729,740

(22) Filed: Dec. 5, 2003

(65) Prior Publication Data

US 2004/0178804 A1 Sep. 16, 2004

Related U.S. Application Data

(63) Continuation-in-part of application No. 10/389,036, filed on Mar. 14, 2003.

(51) Int. Cl.⁷ .......................... G01R 27/26; G01R 27/08
(52) U.S. Cl. ...................................... 324/663; 324/691
(58) Field of Search ............................... 324/691–698, 324/519, 439, 658, 686, 464

(56) References Cited

U.S. PATENT DOCUMENTS

| 3,636,444 A | 1/1972 | Strawn et al. ............. 324/61 R |
| 3,778,706 A | 12/1973 | Thompson ................. 324/61 R |
| 4,031,742 A | * 6/1977 | Michael et al. .............. 73/40.7 |

(Continued)

OTHER PUBLICATIONS

U.S. Appl. No. 10/456,378, filed Jun. 6, 2003, Centanni, entitled: Method and Apparatus for Formulating and Controlling Chemical Concentrations in a Solution.
U.S. Appl. No. 10/456,380, filed Jun. 6, 2003, Centanni, entitled: Method and Apparatus for Formulating and Controlling Chemical Concentrations in a Gas Mixture.
U.S. Appl. No. 10/667,988, filed Sep. 22, 2003, Korenev et al., entitled: Method and Apparatus for Measuring the Concentration of Hydrogen Peroxide in a Fluid.
T. J. Buckley et al., "Toroidal Cross Capacitor for Measuring the Dielectric Constant of Gases," Review of Scientific Instruments, vol. 71, No. 7, Jul. 2000, pp. 2914–2921.
Gross et al., "The Dielectric Constants of Water Hydrogen Peroxide and Hydrogen Peroxide–Water Mixtures, " L. Amer. Chem. Soc., vol. 72, 1950, pp. 2075–2080.
"Humidity Sensor Theory and Behavior," Psychometrics and Moisture, Honeywell HVAC, Nov. 27, 2002.

(Continued)

*Primary Examiner*—N. Le
*Assistant Examiner*—Amy He
(74) *Attorney, Agent, or Firm*—Kusner & Jaffe; Michael A. Centanni

(57) ABSTRACT

A contaminant detecting system for determining the presence of a miscible or immiscible contaminant in a fluid. The fluid acts as a dielectric between the plates of a capacitive sensing element. The measured capacitance value varies in accordance with the composition of the fluid, to indicate the presence or absence of the contaminant in the fluid.

14 Claims, 9 Drawing Sheets

U.S. PATENT DOCUMENTS

| | | | | |
|---|---|---|---|---|
| 4,219,776 | A | | 8/1980 | Arulanandan ................ 324/323 |
| 4,427,772 | A | | 1/1984 | Kodera et al. ................ 435/27 |
| 4,509,522 | A | | 4/1985 | Manuccia et al. .......... 128/634 |
| 4,525,265 | A | | 6/1985 | Abe et al. .................... 204/403 |
| 4,674,879 | A | | 6/1987 | Gregorig et al. ............ 356/301 |
| 4,857,152 | A | | 8/1989 | Armstrong et al. ......... 204/1 T |
| 5,151,660 | A | | 9/1992 | Powers et al. .............. 324/689 |
| 5,157,968 | A | | 10/1992 | Zfira ........................... 73/149 |
| 5,171,523 | A | | 12/1992 | Williams ..................... 422/20 |
| 5,243,858 | A | | 9/1993 | Erskine et al. ........... 73/204.26 |
| 5,364,510 | A | | 11/1994 | Carpio .................... 204/153.1 |
| 5,439,569 | A | | 8/1995 | Carpio .................... 204/153.1 |
| 5,459,568 | A | | 10/1995 | Yano et al. ................. 356/336 |
| 5,470,754 | A | * | 11/1995 | Rounbehler et al. ......... 436/106 |
| 5,600,142 | A | | 2/1997 | Van Den Berg et al. ..................... 250/339.13 |
| 5,847,276 | A | | 12/1998 | Mimken et al. .............. 73/453 |
| 5,882,590 | A | | 3/1999 | Stewart et al. ................ 422/28 |
| 5,997,685 | A | | 12/1999 | Radhamohan et al. ...... 156/345 |
| 6,162,409 | A | | 12/2000 | Skelley et al. ........... 423/239.1 |
| 6,369,387 | B1 | | 4/2002 | Eckles ........................ 250/343 |
| 6,454,874 | B1 | | 9/2002 | Jacobs et al. ................ 134/18 |
| 6,614,242 | B2 | * | 9/2003 | Matter et al. ................ 324/698 |
| 6,660,231 | B2 | * | 12/2003 | Moseley ....................... 422/98 |
| 6,706,648 | B2 | | 3/2004 | Yamazaki et al. .......... 438/790 |
| 2002/0014410 | A1 | | 2/2002 | Silveri et al. ................ 204/412 |
| 2002/0033186 | A1 | | 3/2002 | Verhaverbeke et al. ........ 134/26 |
| 2002/0076492 | A1 | | 6/2002 | Loan et al. ............ 427/255.28 |
| 2002/0109511 | A1 | * | 8/2002 | Frank ......................... 324/663 |
| 2002/0111040 | A1 | | 8/2002 | Yamzaki et al. ............ 438/783 |
| 2002/0157686 | A1 | | 10/2002 | Kenny et al. ............... 134/1.3 |
| 2003/0063997 | A1 | | 4/2003 | Fryer et al. ..................... 422/3 |
| 2003/0102007 | A1 | | 6/2003 | Kaiser ........................... 134/1 |
| 2003/0157587 | A1 | | 8/2003 | Gomez et al. ................. 435/30 |
| 2004/0029257 | A1 | | 2/2004 | Dutil et al. .................. 435/266 |
| 2004/0079395 | A1 | | 4/2004 | Kim et al. ..................... 134/30 |
| 2004/0178802 | A1 | | 9/2004 | Centanni ..................... 324/662 |
| 2004/0178803 | A1 | | 9/2004 | Centanni ..................... 324/662 |
| 2004/0262170 | A1 | | 12/2004 | Centanni ..................... 205/782 |

OTHER PUBLICATIONS

Philipp, "*Charge Transfer Sensing,*" 1997.

Wojslaw, "*Everything You Wanted to Know About Digitally Programmable Potentiometers,*" Catalyst Semiconductor, Inc., Oct. 17, 2001, Publication No. 6009.

Kittel, "*Introduction to Solid State Physics,*" Fourth Edition, John Wiley & Sons, Inc., 1971.

Philipp, "*The Charge Transfer Sensor,*" Sensors Magazine, Oct. 1999.

U.S. Appl. No. 10/872,227, filed Jun. 18, 2004, Kaiser et al., entitled: Method and Apparatus for Monitoring the Purity and/or Quality of Steam.

U.S. Appl. No. 10/896,609, filed Jul. 21, 2004, Kaiser et al., entitled: Method and Apparatus for Real Time Monitoring of Metallic Cation Concentrations in a Solution.

U.S. Appl. No. 10/900,745, filed Jul. 28, 2004, Kaiser et al., entitled: Method and Apparatus for Monitoring the State of a Chemical Solution for Decontamination of Chemical and Biological Warfare Agents.

U.S. Appl. No. 10/931,186, filed Aug. 31, 2004, Kaiser et al., entitled: Method and Apparatus for Monitoring Detergent Concentration in a Decontamination Process.

* cited by examiner

US 6,897,661 B2

METHOD AND APPARATUS FOR DETECTION OF CONTAMINANTS IN A FLUID

RELATED APPLICATIONS

This application is a continuation-in-part of U.S. application Ser. No. 10/389,036, filed Mar. 14, 2003, and hereby fully incorporated herein by reference.

FIELD OF THE INVENTION

The present invention relates generally to the field of biocontamination deactivation, and more particularly to a method and apparatus for detecting the presence of contaminants in a fluid.

BACKGROUND OF THE INVENTION

The degree of polarity of a molecule is expressed in terms of a "dipole moment." Molecules, such as water, that exhibit a separation of charge within the molecule, have non-zero dipole moments. If the separated charges are equal in magnitude but opposite in sign, the magnitude of the dipole moment is equal to the product of the value of one of the separated charges and the distance of separation between the charges. The dipole moment is a vector that points from the negatively charged side of the molecule to the positively charged side of the molecule. The dipole moment depends on three factors, namely, (1) polarity of the molecule, (2) the magnitude of the separated charge, and (3) the geometry of the molecule. It is known that different molecules will have different dipole moments.

The present invention uses differences in the dipole moments of different molecules as a means for detecting the presence of contaminants in a fluid.

SUMMARY OF THE INVENTION

In accordance with the present invention, there is provided a contaminant detecting system for determining the presence of a contaminant in a fluid, comprising: (a) a capacitor having first and second conducting plates, said fluid being a dielectric therebetween; and (b) sensing means for sensing a change in an electrical property of the capacitor, said change in the electrical property varying according to the presence of the contaminant in the fluid.

In accordance with another aspect of the present invention, there is provided a method for determining the presence of a contaminant in a fluid, comprising the steps of: (a) passing the fluid between a capacitor having first and second conducting plates, said fluid being a dielectric therebetween; and (b) determining a change in an electrical property of the capacitor, said change in the electrical property varying according to the presence of the contaminant in the fluid.

An advantage of the present invention is the provision of a method and apparatus for detecting the presence of contaminants in a fluid by using the fluid as dielectric material of a capacitor.

Another advantage of the present invention is the provision of a method and apparatus for detecting the presence of contaminants in a fluid by detecting changes in an electrical property of a capacitor exposed to the fluid.

Yet another advantage of the present invention is the provision of an apparatus for detecting the presence of contaminants in a fluid that is simple and inexpensive to manufacture.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
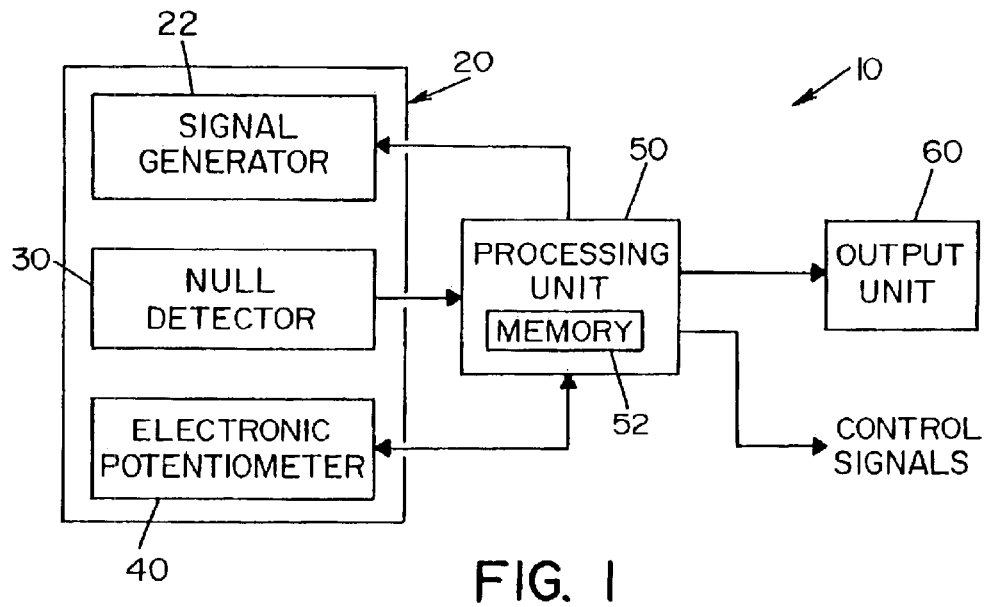
FIG. 1 is a block diagram of a system for detecting chemical concentrations.

Referring now to the drawings wherein the showings are for the purposes of illustrating a preferred embodiment of the invention only and not for purposes of limiting same, FIG. 1 shows a chemical concentration detecting system 10. Detecting system 10 is generally comprised of a sensor circuit 20, a processing unit 50 and an output unit 60.

Sensor circuit 20 uses a capacitor to sense concentration of chemicals in a multi-component fluid, as will be described in detail below. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules.

In a preferred embodiment, processing unit 50 may take the form of a microcomputer or microcontroller, including a memory 52 for data storage. Processing unit 50 may also be used to control the operation of other system elements, such as flow controls for controlling fluid flow of components of a decontamination solution. Output unit 60 provides information in an audible and/or visual form. Accordingly, output unit 60 may take the form of an audio speaker and/or visual display unit.

Figure 2:
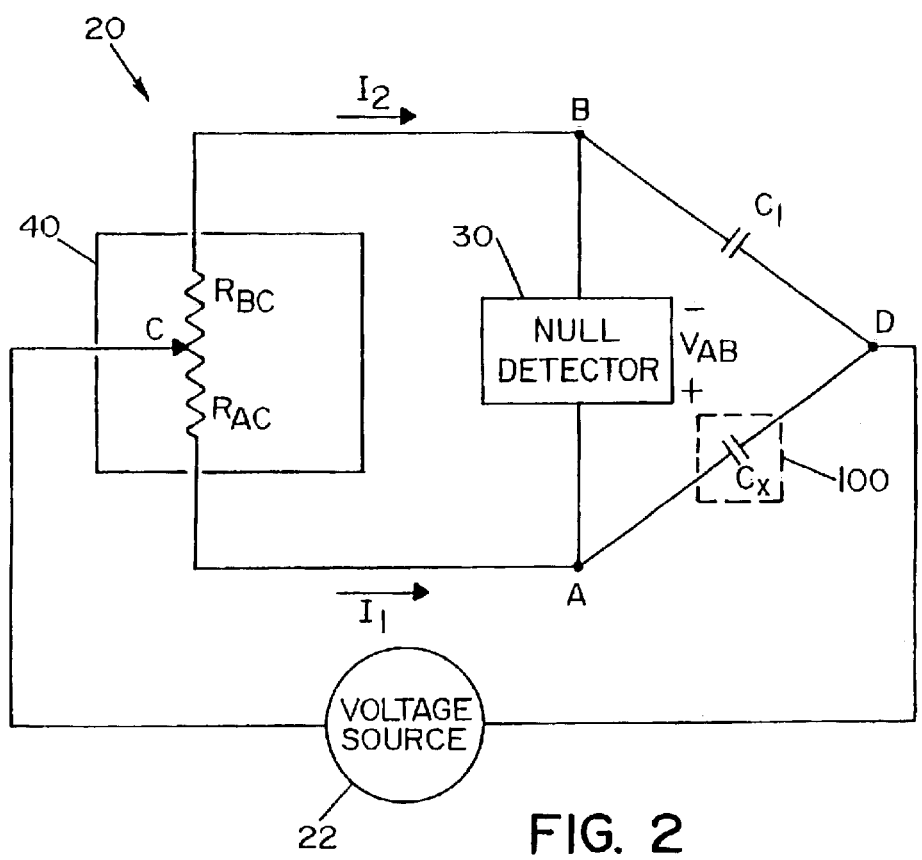
FIG. 2 is a schematic illustrating a sensor circuit, according to a first embodiment.

Referring now to FIG. 2, there is shown a detailed schematic of sensor circuit 20. In the preferred embodiment, sensor circuit 20 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. In the preferred embodiment, the bridge circuit is used to determine a capacitance value indicative of the concentration of chemicals in a multi-component fluid. In the embodiment shown in FIG. 2, sensor circuit 20 is generally comprised of a voltage source 22, a null detector 30, an electronic potentiometer 40, a capacitor $C_1$ of known capacitance, and a capacitor $C_x$. Capacitor $C_1$ is conventional capacitor located outside vessel, tank or chamber 100.

Capacitor $C_x$ may be directly exposed to a decontamination solution having multiple chemical components. In this regard, capacitor $C_x$ is located in a vessel, tank or chamber 100, wherein the decontamination solution fills the gap between the conducting plates of capacitor $C_x$, thereby acting as the insulator or "dielectric" of capacitor $C_x$. Sensor circuit 20 provides data indicative of a capacitance $C_x$, corresponding to a chemical concentration. In this regard, capacitance $C_x$ will vary in accordance with the concentration of components in the multi-component fluid. It should be appreciated that the conducting plates may also be located such that they are not directly exposed to the decontamination solution, but the decontamination solution still acts as a dielectric between the conduction plates.

In a preferred embodiment, capacitor $C_x$ is a parallel plate capacitor. However, it should be appreciated that capacitor $C_x$ could be constructed in a different form. For example, $C_x$ could be a cylindrical or spherical capacitor. If a spherical capacitor is used as capacitor $C_x$, holes must be placed in the outer shell of the capacitor such that the chemical components can enter and exit the capacitor.

Electronic potentiometer 40 functions in the same manner as a mechanical potentiometer. In this regard, electronic potentiometer 40 is a three terminal device. Between two of the terminals is a resistive element. The third terminal known as the "wiper" is connected to various points along the resistive element. The wiper is digitally controlled by processing unit 50 (see FIG. 1). The wiper divides the resistive element into two resistors $R_{BC}$ and $R_{AC}$. Electronic potentiometer 40 may take the form of a digitally programmable potentiometer (DPP™) available from Catalyst Semiconductor, Inc. of Sunnyvale, Calif.

In a first embodiment, voltage source 22 provides an AC voltage signal, such as a sinusoidal or pulse waveform. Null detector 30 is a device for detecting a null condition (i.e., a short circuit), such as a galvanometer, a voltmeter, a frequency-selective amplifier, and the like.

Operation of sensor circuit 20 will now be described in detail. The elements of the bridge circuit are connected between junctions AC, BC, AD, and BD. Electronic potentiometer 40 is operated by processing unit 50 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC}=V_{BC}, \text{ and } V_{AD}=V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC}=V_{BD}/V_{BC}$$

$$V_{AD}=V_{BD}/(V_{AC}/V_{BC})$$

The capacitance of capacitor $C_x$ is connected between junctions A and D with a known capacitance of capacitor $C_1$ between junctions B and D. Electronic potentiometer 40, connected from junction A to junction C to junction B, is adjusted by processing unit 50 to vary the voltages $V_{AC}$ and $V_{BC}$.

When a null is detected by null detector 30, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC}=I_1 R_{AC} \text{ and } V_{BC}=I_2 R_{BC}.$$

The voltage across a capacitor with capacitance C, current I, and frequency is:

$$V = \frac{I}{2\pi f C}$$

Therefore, the voltages $V_{AD}$ and $V_{BD}$ may be expressed as:

$$V_{AD} = \frac{I_1}{2\pi f C_x}$$

$$V_{BD} = \frac{I_2}{2\pi f C_1}$$

As discussed above, $V_{AD}=V_{BD}/(V_{AC}/V_{BC})$, $V_{AC}=I_1 R_{AC}$, and $V_{BC}=I_2 R_{BC}$. Therefore, $$C_x = C_1\left(\frac{R_{BC}}{R_{AC}}\right).$$

In view of the forgoing relationship, when a null condition is detected, the resistance values for $R_{BC}$ and $R_{AC}$, along with the known capacitance value of capacitor $C_1$, can be used to determine unknown value of capacitance for capacitor $C_x$.

Chemical concentration detecting system 10 utilizes differences in dipole moments of different molecules to determine the relative concentration of a chemical in a solution. As discussed above, the decontamination solution fills the gap between the conducting plates of capacitor $C_x$, thereby acting as the dielectric of capacitor $C_x$. By configuring capacitor $C_x$ as an element of a bridge circuit, a measure of resistance values $R_{AC}$ and $R_{BC}$, when the bridge is balanced or nulled, can be used to determine the capacitance of capacitor $C_x$. The capacitance of capacitor $C_x$ is indicative of the relative concentrations of the chemical components in the decontamination solution, since the permittivity of the respective dielectric is affected by the relative concentrations of the chemical components of the decontamination solution.

It is well known that for a parallel plate capacitor $C=(k\epsilon_0)(A/d)=(\epsilon)(A/d)$, where C is capacitance, k is the dielectric constant, $\epsilon_0$ is the permittivity of free space ($8.85\times10^{-12}$ F/m), $\epsilon$ is the permittivity (Farads/meter) of the capacitor dielectric, A is the area of the capacitor plates (m$^2$), and d is the separation in meters between the capacitor plates. As $\epsilon$ increases, the capacitance C will increase. Where the capacitor is a parallel plate capacitor with circular plates of diameter D, C=($\pi$D$^2\epsilon$)/(4d).

It will be appreciated that the dielectric constant k of the capacitor can be determined according to the following expression:

$$k = \frac{4dC}{\pi D^2 \varepsilon_0},$$

where the value of capacitance, C, is determined as discussed above. The dielectric constant of the capacitor can also be determined by determining the capacitance with the dielectric in place between the conducting plates (C$_d$), and then determine the capacitance without the dielectric in place (C$_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance (X$_c$) is a function of frequency. Capacitive reactance is the opposition offered to the flow of alternating current by pure capacitance, and is expressed in ohms (X$_c$=1/(2$\pi$fC)). Accordingly, frequency of the waveform generated by voltage source 22 influences the response of capacitors. Thus, the frequency selected for voltage source 22 should preferably be a frequency that will provide a generally linear response for capacitance as the concentration of a chemical component is varied. This will facilitate the use of interpolation and extrapolation of capacitance values, as will be discussed further below. If a suitable linear response is not obtained, then an expanded set of data points should be stored in memory 52.

Figure 3:
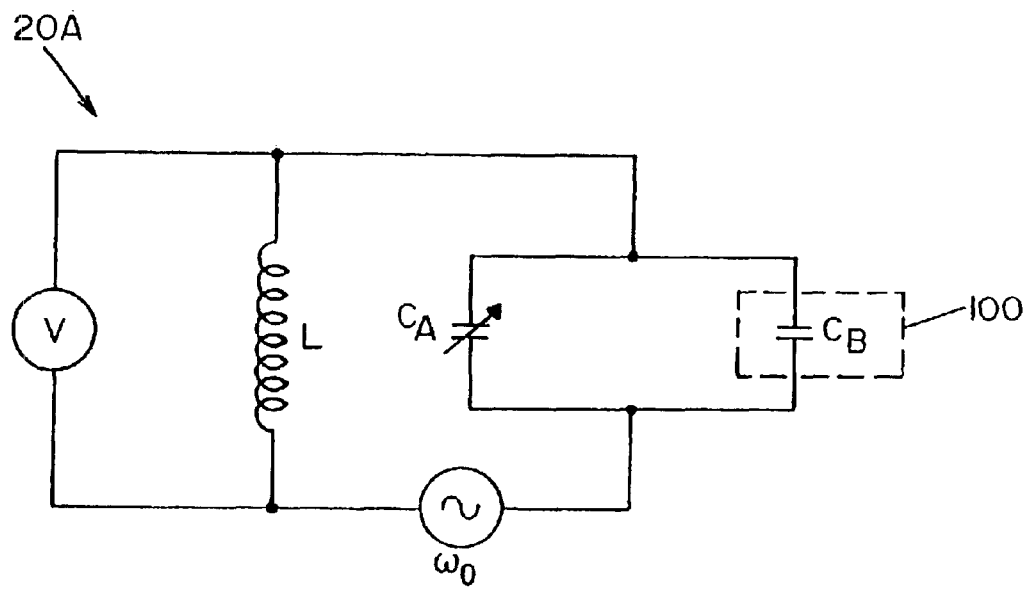
FIG. 3 is a schematic illustrating a sensor circuit, according to a second embodiment.

It should be appreciated that while one embodiment of the present invention includes a sensor circuit 20 in the form of a bridge circuit, other types of circuits and techniques (including other types of bridge circuits, and capacitance meters) known to those skilled in the art, may be suitably used to measure capacitance. For example, FIG. 3 illustrates an alternative sensor circuit 20A. Sensor circuit 20A is an LC resonant circuit, having a variable capacitor C$_A$ located outside vessel 100, and a capacitor C$_B$ directly exposed to a decontamination solution having multiple chemical components. In this regard, capacitor C$_B$ is located in vessel 100, wherein the decontamination solution fills the gap between the conducting plates of capacitor C$_B$, thereby acting as the insulator or "dielectric" of capacitor C$_B$. Since the resonance frequency $\omega_0$=[L(C$_A$+C$_B$)]$^{-1/2}$, the unknown capacitance of capacitor C$_B$ can be determined.

It is recognized that in some cases, the capacitance of the capacitor exposed to the solution located in chamber 100 may be in the range of femtoFarad capacitance to low picoFarad capacitance (e.g., 1 fF to 100 pF), and that changes in concentration of a chemical component in the solution may only result in a change of capacitance in the range of low picoFarad capacitance or even femtoFarad capacitances. Accordingly, the sensor circuit used to measure capacitance may need to have high sensitivity to allow for measurement of small values of capacitance.

Figure 4:
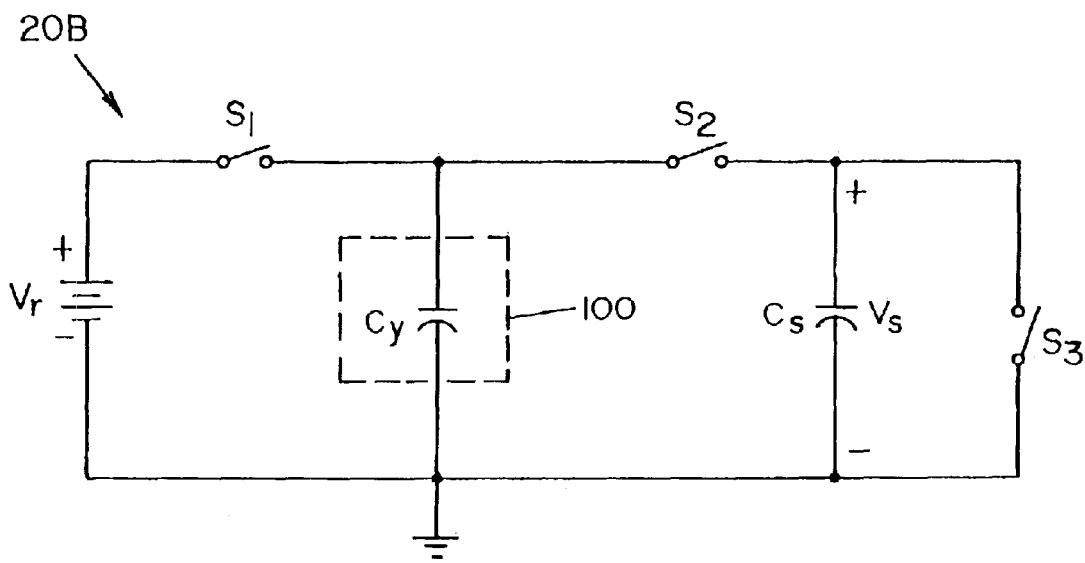
FIG. 4 is a schematic illustrating a sensor circuit according to a third embodiment.

FIG. 4 illustrates yet another alternative sensor circuit 20B suitable for use in connection with the present invention. Sensor circuit 20B is a "charge transfer" sensor circuit. Charge transfer sensor circuits are recognized to provide resolutions of fractions of a femtoFarad. In a charge transfer sensor circuit the unknown capacitance of a sense electrode is determined by charging the sense electrode to a fixed potential, and then transferring that charge to a charge detector comprising a capacitor of known capacitance. In sensor circuit 20B, capacitor C$_y$ of unknown capacitance is located in chamber 100, wherein the solution fills the gap between the conducting plates of capacitor C$_y$, thereby acting as an insulator or "dielectric" of capacitor C$_y$. Capacitor C$_y$ is first connected to a DC reference voltage (V$_r$) via a switch S$_1$. Switch S$_1$ is reopened after C$_y$ is satisfactorily charged to the potential of V$_r$. Then, after as brief as possible a delay so as to minimize leakage effects caused by conductance, switch S$_2$ is closed and the charge (Q) present on C$_y$ is transferred to capacitor C$_s$ (i.e., the charge detector). Once the charge Q is satisfactorily transferred to capacitor C$_s$, switch S$_2$ is reopened. By reading voltage V$_s$, the capacitance of capacitor C$_y$ can be determined. V$_s$ may be input to an amplifier to provide the scaling necessary to present an analog-to-digital converter (ADC) with a useful range of voltage for digital processing. Switch S$_3$ acts as a reset means to reset the charge between charge transfer cycles, so that each charge transfer cycle has a consistent initial condition. Switches S$_1$, S$_2$ and S$_3$ may be electromechanical switches or transistors. Preferably, digital control logic is used to control switches S$_1$, S$_2$ and S$_3$. In a preferred embodiment, C$_s$ is selected to be significantly larger that C$_y$.

The equations governing sensor circuit 20B are as follows:

$V_s=V_r[C_y/(C_y+C_s)]$, therefore $C_y=V_sC_s/[V_r-V_s]$.

The charge-transfer sensor has been applied in a self-contained capacitance-to-digital-converter (CDC) integrated circuit (IC). For example, Quantum Research Group produces a QProx™ CDC sensor IC (e.g., QT300 and QT301 CDC sensor ICs) for detecting femtofarad level changes in capacitance. The CDC sensor IC outputs a digital value corresponding to the detected input capacitance. The value of an external sampling capacitor controls the gain of the sensor.

Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from 10$^{-7}$ pF to 10 $\mu$F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

With reference to FIGS. 1 and 2, operation of chemical concentration detecting system 10 will now be described in detail. As a preliminary step, processing unit 50 stores in memory 52 a set of data comprising values of the capacitance of capacitor C$_x$ for a plurality of relative concentrations of a multi-component decontamination solution. This set of data may be determined by exposing capacitor C$_x$ of system 10 to several different combinations of relative concentrations of the multi-component decontamination solution, and recording the corresponding measured capacitance $C_x$. For example, processing unit 50 may store values of the capacitance of capacitor $C_x$ that are determined for a plurality of relative concentrations of a multi-component decontamination solution comprised of only two components. As the relative concentrations of the first and second components are varied, the corresponding capacitance of capacitor $C_x$ is determined, and stored in memory 52. For instance, capacitance of capacitor $C_x$ may be determined for various concentrations of a first component and a second component (at a fixed volume of the decontamination solution), including, but not limited to:

0% first component and 100% second component,
25% first component and 75% second component,
50% first component and 50% second component,
75% first component and 25% second component, and
100% first component and 0% second component.

After the set of data is stored in memory 52, measurement of concentrations of a multi-component decontamination solution can commence. Capacitor $C_x$ is exposed to a multi-component decontamination solution that is being monitored. As indicated above, capacitor $C_x$ may be located in a vessel, tank or chamber 100 filled with the multi-component solution. A determination of $R_{AC}$ and $R_{BC}$ when the bridge is nulled is then used to determine a value for the capacitance of capacitor $C_x$. As discussed above, $C_x = C_1 (R_{BC}/R_{AC})$. The data stored in memory 52 is searched for the capacitance of capacitor $C_x$ to obtain the corresponding relative concentrations. A linear relationship between concentration and capacitance allows one to normalize any measurement made so as to provide the absolute concentration of each component in the solution. If the capacitance of capacitor $C_x$ is not found in the pre-stored data, the stored data may be interpolated or extrapolated to obtain a concentration corresponding to the measure capacitance of capacitor $C_x$. As noted above, frequency of the waveform generated by voltage source 22 will influence the response of capacitors. Where the capacitance of capacitor $C_x$ does not exhibit a suitable linear response, an expanded set of data points should be stored in memory 52, so that interpolation or extrapolation is unnecessary.

It is also contemplated that a measure of other electrical properties of a capacitor may be used to determine relative concentrations, including, but not limited to, the permittivity and dielectric constant of the capacitor dielectric.

Based upon the determined relative concentrations, processing unit 50 may be programmed to control the concentration of one or more components of the decontamination solution. For instance, processing unit 50 may output control signals (see FIG. 1) to adjust a flow control valve or other control means for modifying the relative concentrations. Accordingly, processing unit 50 may provide feedback control to adjust the relative concentrations to correspond with desired relative concentrations that provide optimum decontamination. Processing unit 50 may also output signals to output unit 60 to provide an audible and/or visual indicator when the determined relative concentrations are not within a desired range. The visual indicator may assist an operator by including a display of the relative concentrations or absolute concentration of an oxidant or sterilant as determined by processing unit 50.

In a preferred embodiment, the multi-component decontamination solution is comprised of two components, namely, an antimicrobial chemical and a base fluid. The antimicrobial chemical is the active chemical for a decontamination process, while the base fluid acts as a diluent for the antimicrobial chemical, or as a vehicle or carrier for the antimicrobial chemical.

Examples of antimicrobial chemicals, include, but are not limited to, liquids, such as hydrogen peroxide, peracids such as peracetic acid, and bleach, as well as gases, such as ozone, ammonia, ethylene oxide, fluorine containing chemicals, chlorine containing chemicals, and other highly oxidative gases.

Examples of base fluids, include, but are not limited to, water, de-ionized water, distilled water, an alcohol (e.g., a tertiary alcohol), a glycol-containing chemical compound, and a mixture thereof. Glycol-containing chemical compounds include, but are not limited to, polyethylene glycol, diethylene glycol, triethylene glycol, tetraethylene glycol, glycol ethers, polypropylene glycol, propylene glycol, and combinations thereof.

Some typical combinations of an antimicrobial chemical and a base fluid, include, but are not limited to, hydrogen peroxide and water, bleach and water, ozone and water, peracid and water, peracetic acid and water, alcohol and water, and ozone dissolved in a glycol, or an alcohol, such as a tertiary alcohol.

The principle of the present invention may also be extended to detection of contaminants in a fluid. In accordance with a preferred embodiment of the present invention, a capacitive sensor circuit is used to detect the presence of miscible and immiscible contaminants in a fluid, as will be described in detail below.

Figure 5:
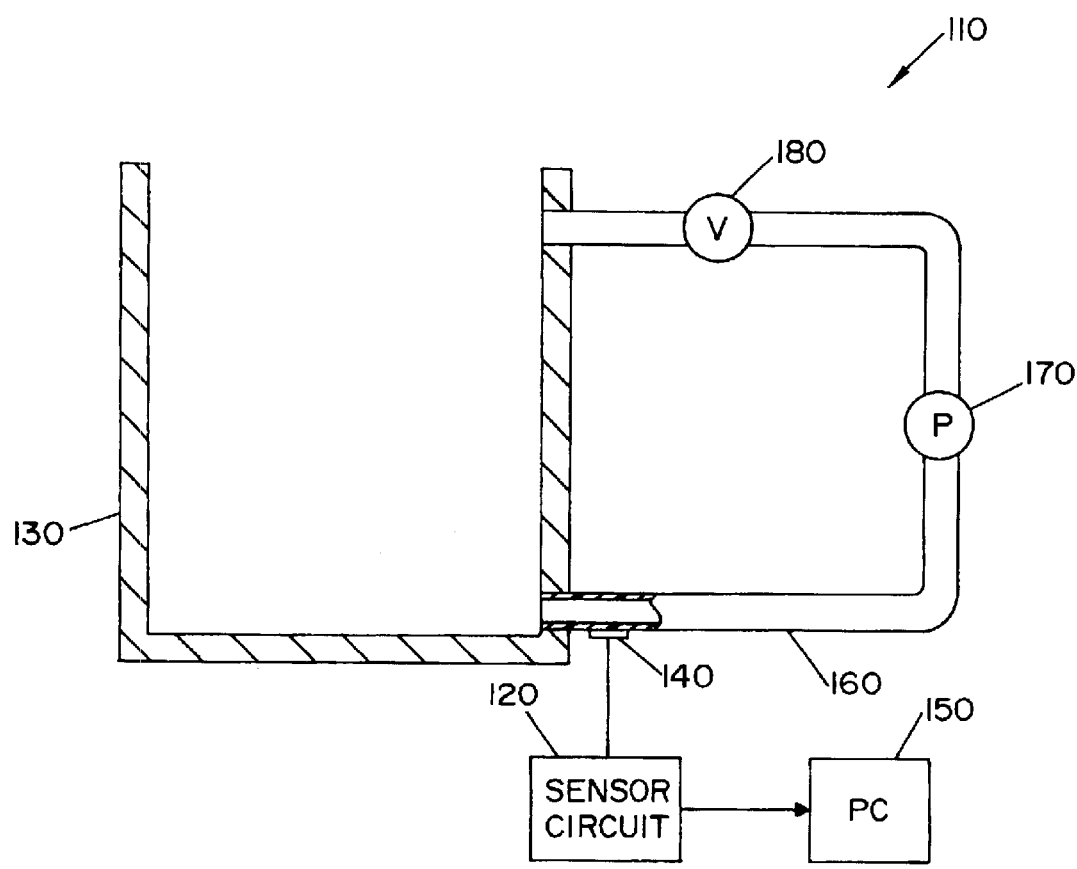
FIG. 5 is a schematic diagram illustrating an apparatus for detecting the presence of contaminants in a fluid.

This aspect of the present invention will first be described with reference to sample data acquired using a test apparatus 110, as shown in FIG. 5. Test apparatus 110 is generally comprised of a capacitive sensor circuit 120, a tank 130, and a recirculation conduit 160.

Tank 130 is a 10L tank with an open top. Conduit 160 provides a fluid path for circulating fluid from the bottom of tank 130 to the top of tank 130. Conduit 160 is made of an electrically nonconductive material. A pump 170 pumps fluid through conduit 160. A restrictor valve 180 is provided along conduit 160 to adjust the flow rate of fluid past capacitive sensing element 140 of sensor circuit 120, described below.

Sensor circuit 120 includes a capacitance sensor and a capacitive sensing element 140. More specifically, sensor circuit 120 includes an E297S board and QTM2000 module, using a charge-transfer capacitance sensor IC QT9701B2, all available from Quantum Research Group Ltd. The charge-transfer capacitance sensor IC outputs a digital value indicative of an input capacitance.

Capacitive sensing element 140 takes the form of a capacitor tape. Capacitor tape is located outside of conduit 160, and serves as a first plate of a sense capacitor. A virtual ground serves as a second plate of the sense capacitor. It should be appreciated that the capacitor tape may also be located inside conduit 160, and act as a floating metallic plate. The size of the metallic plate will effect the sensitivity of sensor circuit 120. For test apparatus 110, the metallic plate of the capacitor tape has approximate rectangular dimensions of 1 inch by 4 inches, and is made of copper.

Digital data indicative of the measured capacitance associated with sensing element 140 is output from sensor circuit 120 to a personal computer (PC) 150. PC 150 includes a software for graphically displaying the collected test data, as will be described below.

The test data was collected by circulating a solution through tank 130 and conduit 160. Miscible and immiscible contaminants were introduced into the circulating solution. Data indicative of the measured capacitance associated with sensing element 140 was graphically displayed before and after the introduction of contaminants.

Figure 6:
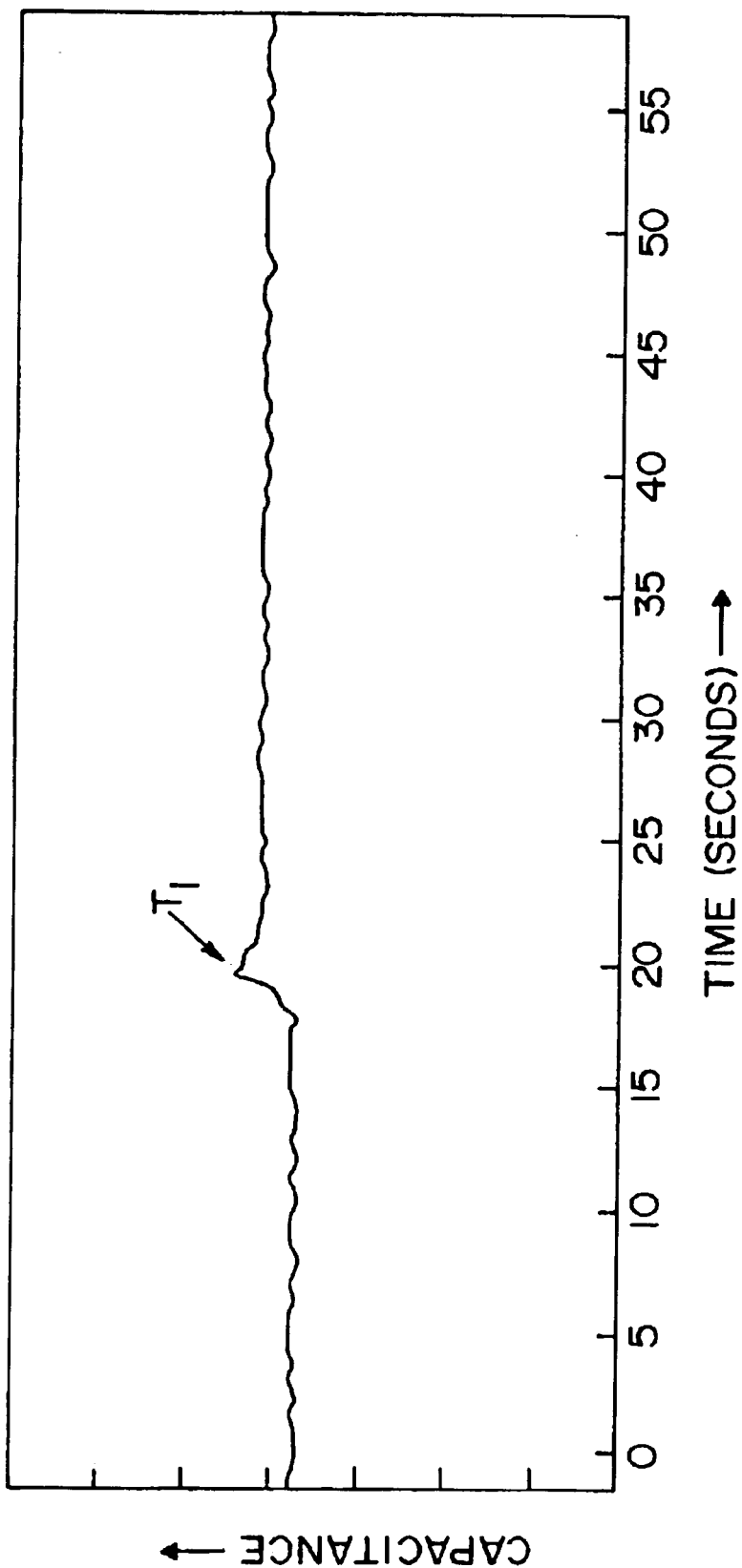
FIG. 6 is a graph of data from a capacitive sensor circuit in a first data collection sample, wherein bovine blood is introduced into a fluid comprised of tap water and saline.

Referring now to FIG. 6, there is shown a first set of test data, showing capacitance as a function of time. For the first set of test data, an initial solution of tap water and saline was introduced into tank 130. At time $T_1$ 5 ml of bovine blood was introduced into conduit 160. It can be observed that the measured capacitance spikes upon introduction of the bovine blood into the solution, and remains elevated as the miscible blood mixes with the tap water and saline.

Figure 7:
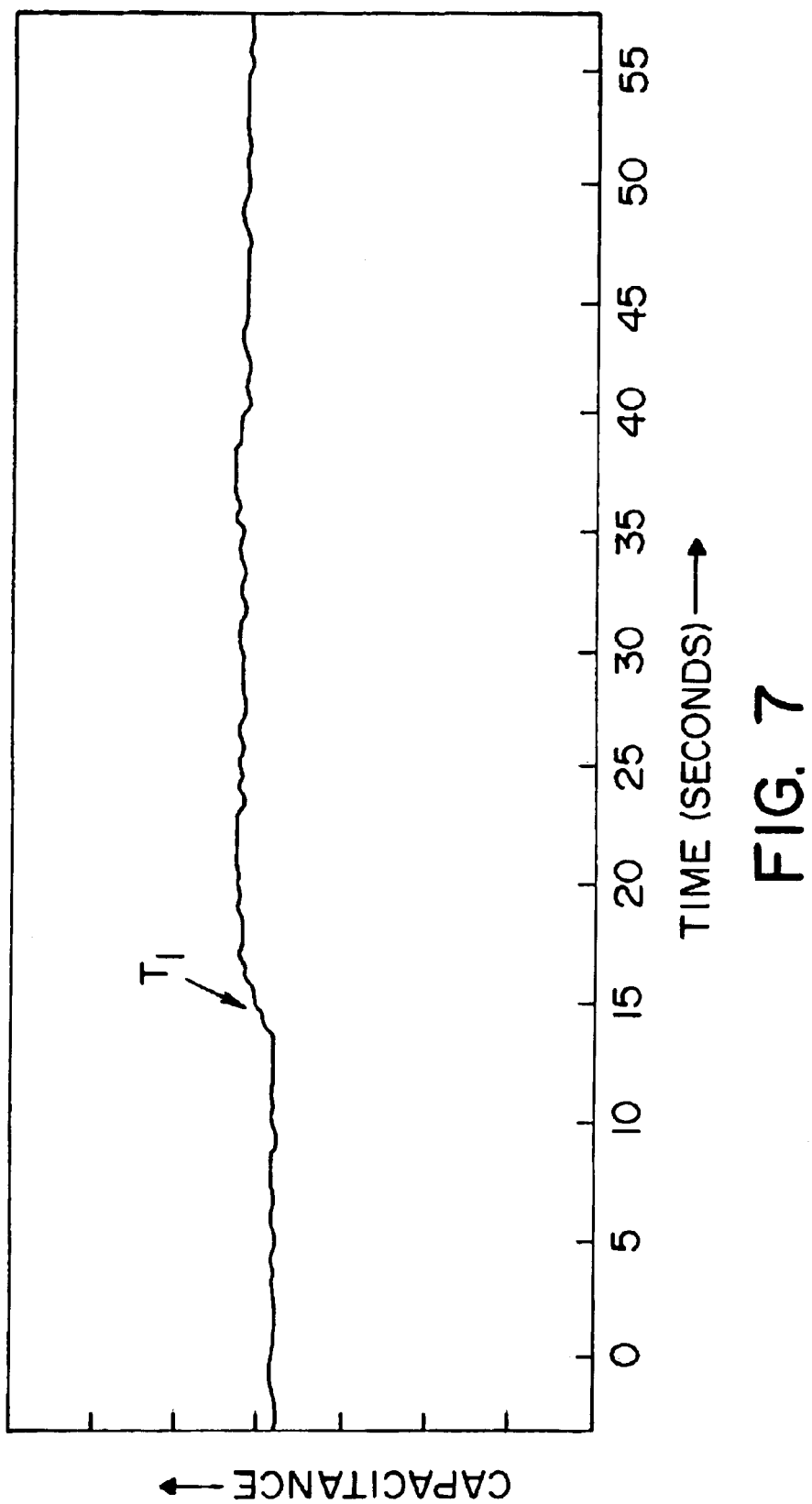
FIG. 7 is a graph of data from a capacitive sensor circuit in a second data collection sample, wherein bovine blood is introduced into a fluid comprised of tap water.

FIG. 7 shows a second set of test data, showing capacitance as a function of time. For the second set of test data, an initial solution of tap water was introduced into tank 130. At time $T_1$ 5 ml of bovine blood was introduced into conduit 160. It can be observed that the measured capacitance increases upon introduction of the bovine blood into the solution, and remains elevated as the miscible blood mixes with the tap water.

Figure 8:
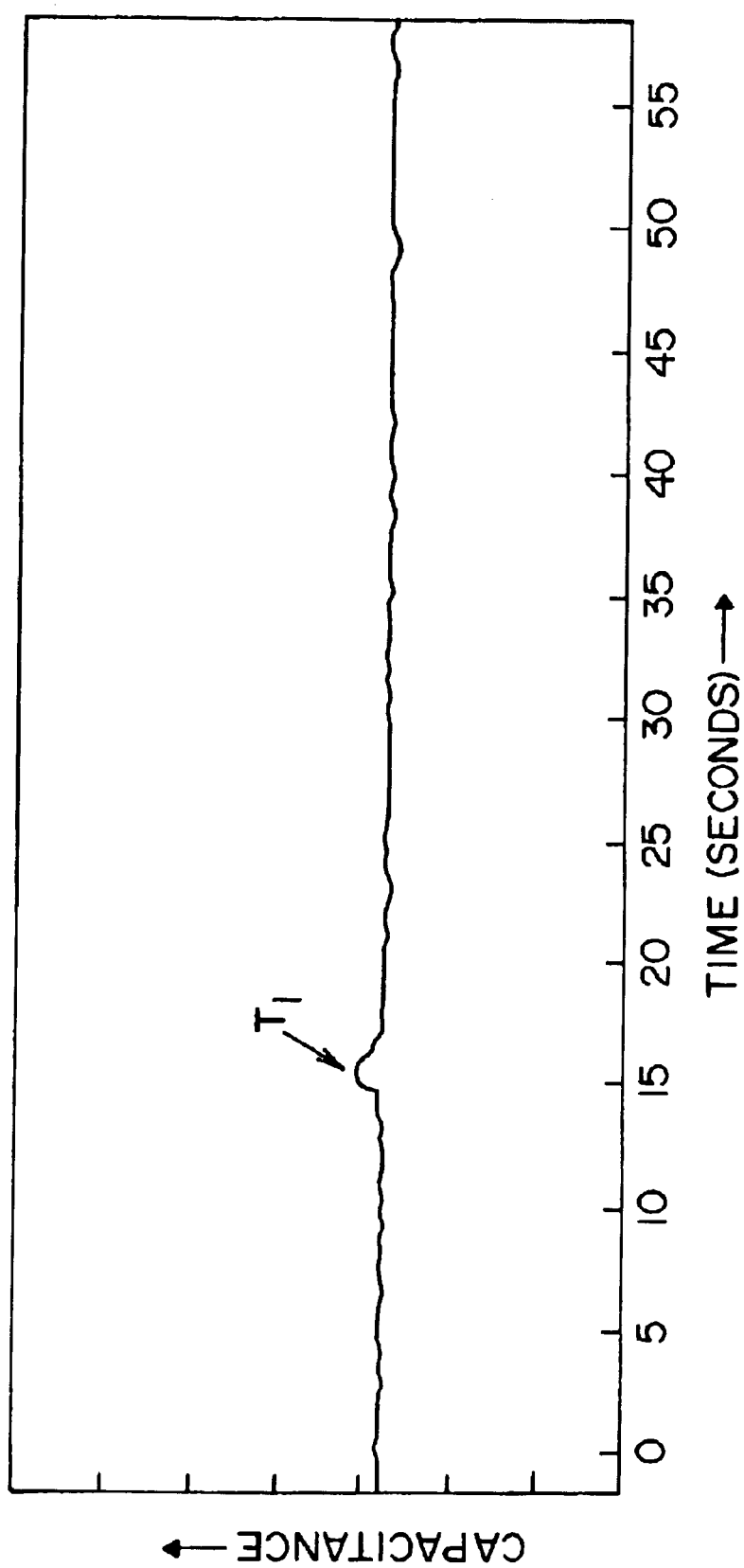
FIG. 8 is a graph of data from a capacitive sensor circuit in a third data collection sample, wherein dirt is introduced into a fluid comprised of tap water.

Referring now to FIG. 8 there is shown a third set of test data, showing capacitance as a function of time. For the third set of test data, an initial solution of tap water was introduced into tank 130. At time $T_1$ approximately 1 gram of dirt was introduced into conduit 160. It can be observed that the measured capacitance "spikes" upon introduction of the dirt, but rapidly returns to the capacitance level observed before the introduction of the dirt.

Figure 9:
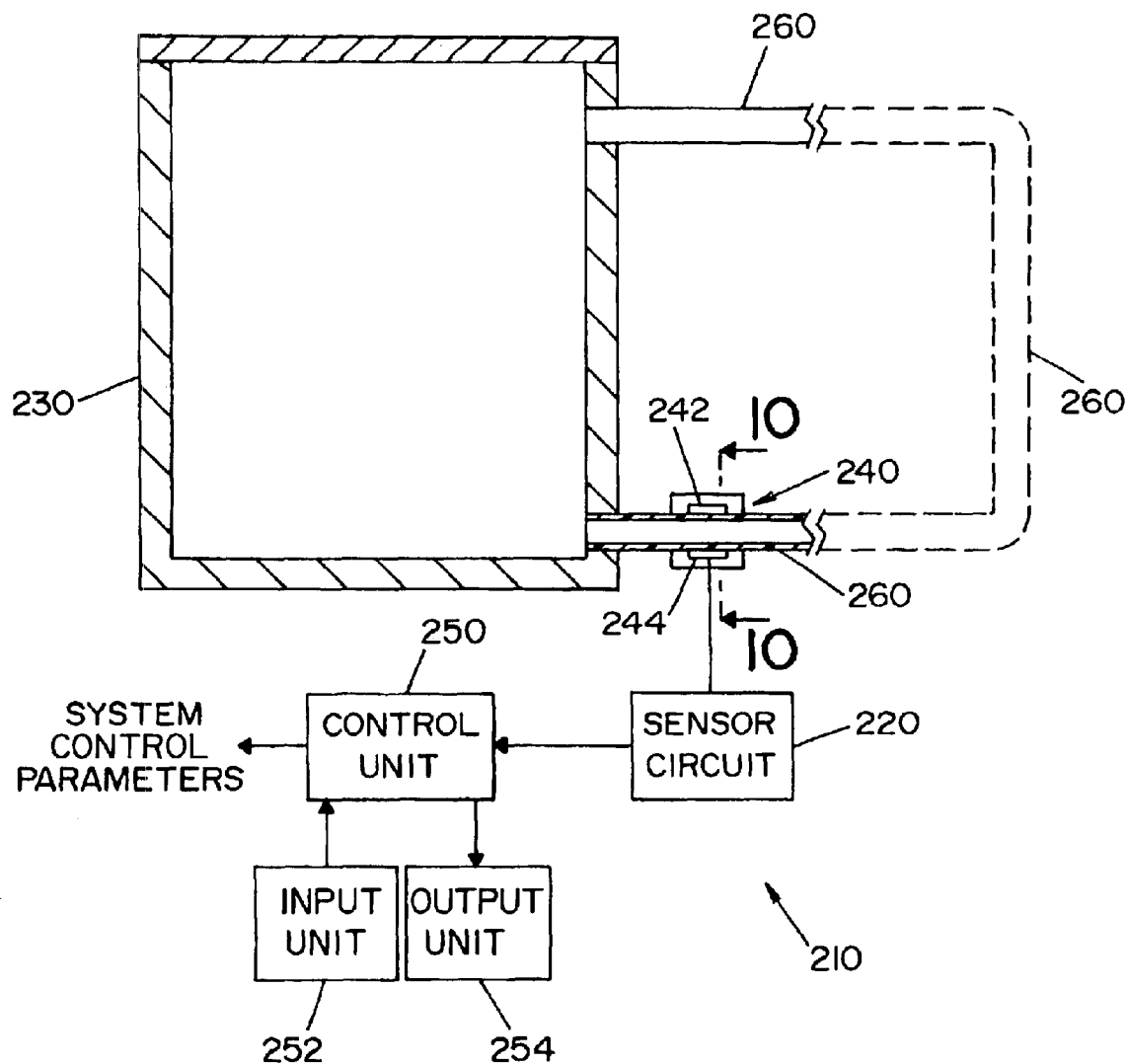
FIG. 9 is a simplified block diagram of a fluid microbial decontamination system including means for detecting the presence of contaminants in a fluid, according to a preferred embodiment of the present invention.

FIG. 9 shows a block diagram of a fluid microbial decontamination system 210 (e.g., a washer disinfector, an endoscope reprocessor, or the like) designed to cause microbes on an article to be removed or killed by a fluid antimicrobial agent. It should be appreciated that the block diagram of fluid microbial decontamination system 210 has been simplified by omitting components of a typical fluid microbial decontamination system, in order to more clearly illustrate the present invention. The fluid microbial decontamination system shown in FIG. 9 is exemplary, and is not intended to limit the scope of the present invention.

System 210 includes a treatment chamber 230, a conduit 260, a capacitive sensor circuit 220, and a control unit 250. Articles to be treated are located in treatment chamber 230. Antimicrobial fluids and rinse solutions are circulated through treatment chamber 230 to treat the articles. The articles subject to treatment are typically re-usable devices used in connection with medical, dental, pharmaceutical and veterinary practices.

Conduit 260 provides a fluid path for circulating fluids through treatment chamber 230. Conduit 260 is preferably interconnected with other conduits (not shown) comprising the plumbing system of system 210. Conduit 260 is preferably made of an electrically nonconductive material, such as plastic or ceramic material.

In a preferred embodiment, sensor circuit 220 includes a charge-transfer capacitance sensor IC and a capacitive sensing element 240, described in detail below. By way of example, and not limitation, the charge-transfer capacitance sensor IC may take the form of model number QT9701B2 from Quantum Research Group Ltd. Alternatively, a capacitance-to-digital-converter (CDC) may be used (e.g., model numbers QT300 and QT301 from Quantum Research Group Ltd.). The charge-transfer capacitance sensor IC and the CDC output a digital value indicative of an input capacitance.

Figure 10:
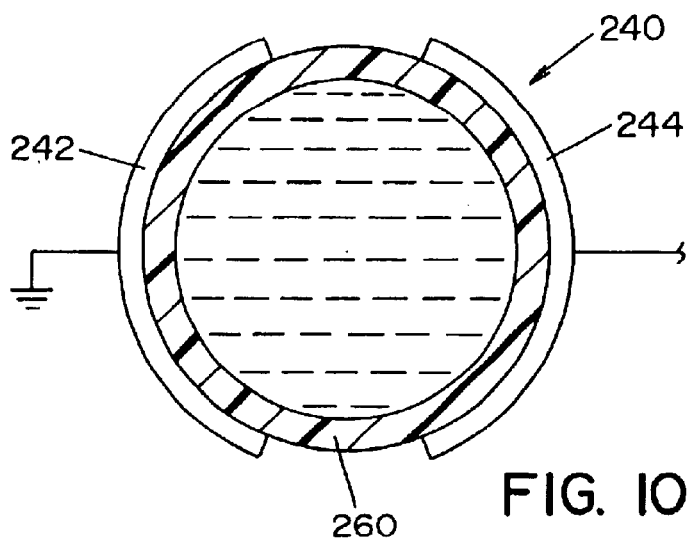
FIG. 10 is a cross-sectional view of a conduit and capacitive sensing element, taken along lines 10—10 of FIG. 9.

As best seen in FIG. 10, sensing element 240 includes a first metal foil electrode 242 and a second metal foil electrode 244. Electrodes 242 and 244 are located along the outer surface of conduit 260, and are preferably made of copper. Electrode 242 is connected to ground, while electrode 244 is connected as an input to sensor circuit 120.

In a preferred embodiment, control unit 250 may take the form of a microcomputer or microcontroller, including a memory (not shown) for data storage. Control unit 250 processes data received from sensor circuit 220, and also controls the operation of other elements of system 210, including, but not limited to, flow controls for controlling fluid flow through treatment chamber 230.

Input unit 252 provides means for inputting data to control unit 250. By way of example, and not limitation, input unit 252 may take the form of a keyboard, a keypad, switches, or a touch screen. Output unit 254 provides information to an operator in an audible and/or visual form. Accordingly, output unit 254 may take the form of an audio speaker and/or visual display unit.

A first mode of operating system 210 will now be described with reference to FIG. 11. Sensor circuit 220 may be suitably used to determine whether a fluid is devoid of any miscible contaminants (e.g., blood, urine, soap, antimicrobial chemicals, miscible soil, and the like). In this regard, the capacitance value provided by sensor circuit 220 will vary in accordance with the composition of the fluid sensed by sensing element 240, as shown in FIGS. 6 and 7.

A capacitance value is established for the fluid devoid of any miscible contaminants. This capacitance value is then used to establish a threshold value. By way of example, and not limitation, the processing cycle may be (1) a wash cycle, (2) an antimicrobial treatment cycle, or (3) a rinse cycle that follows a wash cycle or an antimicrobial treatment cycle. In the case of a wash cycle, a threshold value can be determined for a solution generally comprised of a cleaning agent (e.g., soap and/or detergent), and water. For the antimicrobial treatment cycle, a threshold value can be determined for a solution generally comprised of an antimicrobial treatment chemical (e.g., a sterilant, such as peracetic acid) and a diluent (e.g., water). For a rinse cycle, a threshold value can be determined for a fluid generally comprised of pure water. In each case, the threshold value is established for a fluid having a generally constant concentration of chemical components. It should be appreciated that the threshold value may be determined using the method and apparatus for determining the concentration of chemical components in a fluid, as described above.

Figure 11:
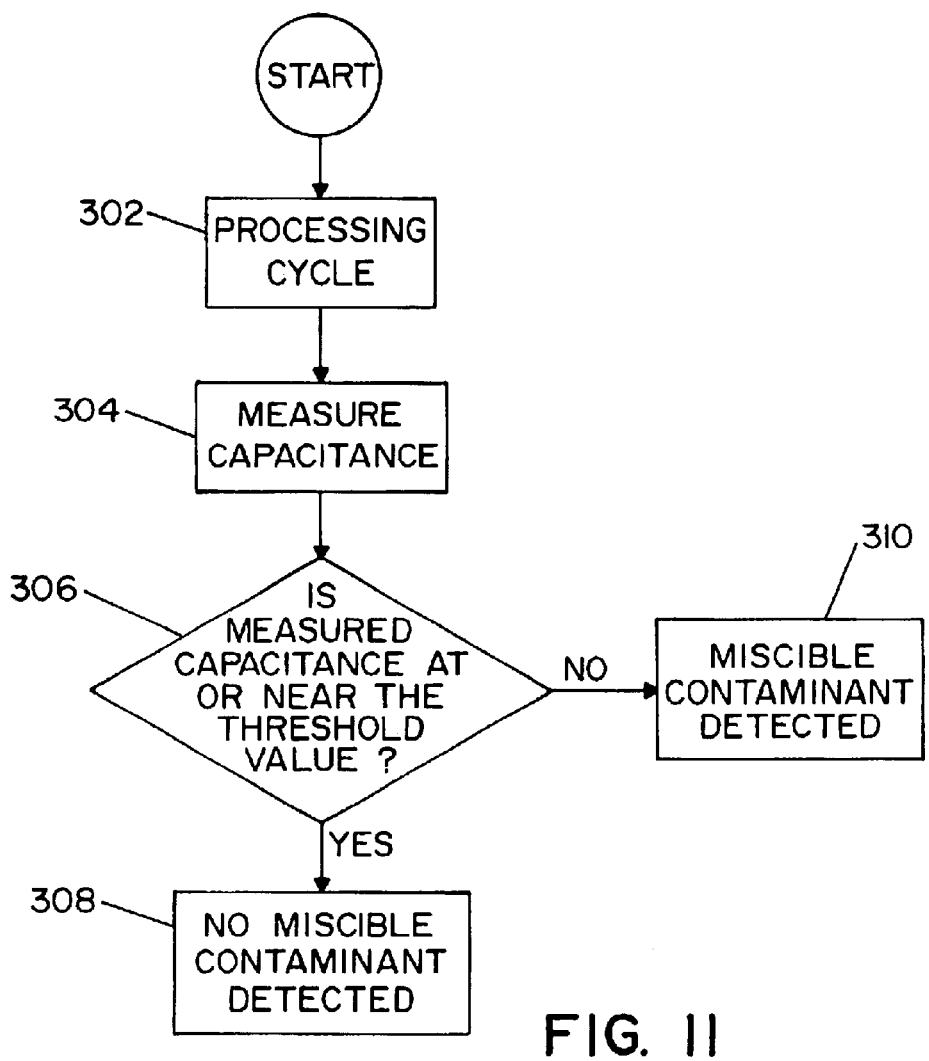
FIG. 11 is a flow diagram illustrating a portion of a control algorithm for a fluid microbial decontamination system, wherein the presence of a miscible contaminant is detected.

Referring now to FIG. 11, a processing cycle commences at step 302. At predetermined intervals during the processing cycle, the capacitance value is measured using sensor circuit 220 (step 304). The measured capacitance value is received by control unit 250. Control unit 250 compares the measured capacitance value to the threshold value, to determine whether the measured capacitance value is at, or near, the threshold capacitance value (step 306).

If the measured capacitance value is at, or near, the threshold capacitance value, control unit 250 determines that the fluid is devoid of a miscible contaminant (step 308). If the measured capacitance value is not at, or near, the threshold capacitance value, control unit 250 determines that a miscible contaminant has been detected (step 310). Accordingly, control unit 250 takes corrective action. For example, control unit 250 may continue with the processing cycle until the miscible contaminant is no longer detected, abort the current processing cycle, or take other corrective action. Control unit 250 may also alert the operator to the detection of a miscible contaminant.

For example, where the processing cycle is a rinse cycle following a wash cycle, blood may be detected in the rinse water if the measured capacitance value is not at, or near, the threshold capacitance value. Upon detecting the presence of the blood in the rinse water, control unit 250 may abort the current rinse cycle and take corrective action, such as commencing a new wash cycle. Accordingly, the present invention can be used to assure that no residual, miscible contaminant is present.

It should be appreciated that rather than determining whether the measured capacitance value is at, or near, the threshold value to detect the presence or absence of a miscible contaminant, it can be determined whether the measured capacitance value is greater (or less) than the threshold capacitance value. A measured value deviating a predetermined amount from the threshold value is indicative of the presence of a miscible contaminant.

A second mode of operating system 210 will now be described with reference to FIG. 12. Sensor circuit 220 may be suitably used to determine whether a fluid is devoid of any immiscible contaminants (e.g., dirt, bone matter, skin, organ tissue, immiscible soil, and the like). In this mode of operation, sensor circuit 220 outputs a signal to control unit 250 indicative of a "spike" in the measured capacitance value to indicate the presence of an immiscible contaminant, as shown in FIG. 8.

A capacitance value is established for the fluid devoid of any immiscible contaminants. This capacitance value is then used to establish a base value. By way of example, and not limitation, the processing cycle may be (1) a wash cycle, (2) an antimicrobial treatment cycle, or (3) a rinse cycle that follows a wash cycle or an antimicrobial treatment cycle. In the case of a wash cycle, a base value can be determined for a solution generally comprised of a cleaning agent (e.g., soap and/or detergent), and water. For the antimicrobial treatment cycle, a base value can be determined for a solution generally comprised of an antimicrobial treatment chemical (e.g., a sterilant, such as peracetic acid) and a diluent (e.g., water). For a rinse cycle, a base value can be determined for a fluid generally comprised of pure water. In each case, the base value is established for a fluid having a generally constant concentration of chemical components. It should be appreciated that the base value may be determined using the method and apparatus for determining the concentration of chemical components in a fluid, as described above.

Figure 12:
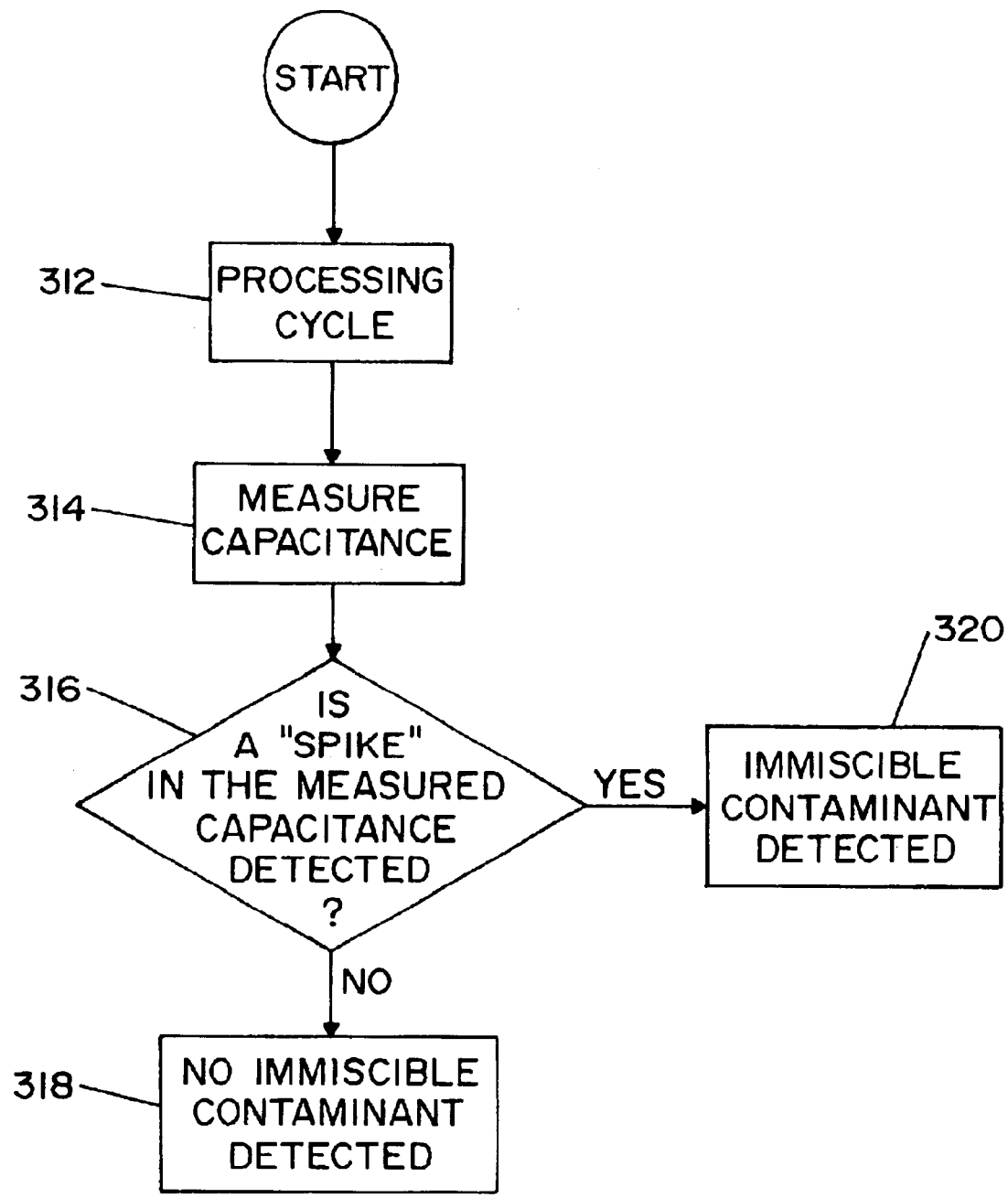
FIG. 12 is a flow diagram illustrating a portion of a control algorithm for a fluid microbial decontamination system, wherein the presence of an immiscible contaminant is detected.

Referring now to FIG. 12, a processing cycle commences at step 312. At predetermined intervals during the processing cycle, the capacitance value is measured using sensor circuit 220 (step 314). Next, it is determined whether a "spike" in the measured capacitance has occurred (step 316). If no "spike" is detected in the measured capacitance value, then it is determined that no immiscible contaminant is present in the fluid (step 318). If a "spike" is detected in the measured capacitance, then it is determined that an immiscible contaminant is present in the fluid (step 320). It should be appreciated that the "spike" is detected as a sudden rise and fall in the measured capacitance value, wherein the measured capacitance value before and after the "spike" is the base value associated with a fluid having a generally constant concentration of chemical components.

In response to detection of a "spike," control unit 250 can take corrective action, or abort the current processing cycle. Control unit 250 may also alert the operator to the detection of an immiscible contaminant. For example, where the processing cycle is a rinse cycle following an antimicrobial treatment cycle, the presence of dirt may be detected in the rinse water by detection of a "spike" in the measured capacitance. Upon detecting the presence of the dirt in the rinse water, control unit 250 may abort the current rinse cycle, and alert the operator to take corrective action, such as commencing a re-wash of the articles subject to the antimicrobial treatment cycle. Accordingly, the present invention can be used to assure that no residual, immiscible contaminant is present.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A contaminant detecting system for determining the presence of a contaminant in a fluid used in a microbial decontamination process, comprising:

a capacitor having first and second conducting elements, said fluid being a dielectric therebetween, and being used to process an article in the microbial decontamination process;

sensing means responsive to a change in an electrical property of the capacitor, said change in the electrical property varying according to the presence of the contaminant in the fluid, said contaminant being removed from said article during the microbial decontamination process; and control means for receiving a measured value from said sensing means indicative of the electrical property of the capacitor, said control means capable of detecting the presence of miscible and immiscible contaminants in the fluid, wherein said control means:

(a) determines the presence of a miscible contaminant in the fluid if the measured value deviates a predetemined amount from a threshold value, and (b) determines the presence of an immiscible contaminant in the fluid if said measured value spikes from a base value during a predetermined time period.

2. A contaminant detecting system according to claim 1, wherein said sensing means includes a sensing circuit for sensing capacitance.

3. A contaminant detecting system according to claim 2, wherein said sensing circuit includes means for generating a digital value indicative of an input capacitance.

4. A contaminant detecting system according to claim 3, wherein said means for generating the digital value indicative of the input capacitance is selected from the group consisting of: a charge-transfer capacitance sensor IC and a capacitance-to-digital-converter (CDC).

5. A contaminant detecting system according to claim 1, wherein said control means includes:

means for comparing said measured value with the threshold value to determine if the measured value deviates a predetermined amount from said threshold value.

6. A contaminant detecting system according to claim 1, wherein said miscible contaminant selected from the group consisting of: blood, urine, and miscible soil.

7. A contaminant detecting system according to claim 1 wherein said immiscible contaminant selected from the group consisting of: dirt, bone matter, skin, organ tissue, and immiscible soil.

8. A contaminant detecting system according to claim 1, wherein said microbial decontamination process is selected from the group consisting of: a washing process, an antimicrobial treatment process and a rinsing process.

9. A method for determining the presence of a contaminant in a fluid used in a microbial decontamination process, comprising:

passing the fluid between a capacitor having first and second conducting elements, said fluid being a dielectric therebetween, and being used to process an article in the microbial decontamination process; and determining a measured value indicative of an electrical property of the capacitor, said electrical property varying according to the presence of the contaminant in the fluid, said contaminant being removed from said article during the microbial decontamination process;

detecting the presence of a miscible contaminant in the fluid if the measured value deviates a predetermined amount from a threshold value, and detecting the presence of an immiscible contaminant in the fluid if the measured value spikes from a base value during a predetermined time period.

10. A method according to claim 9, wherein said electrical property is capacitance.

11. A method according to claim 9, wherein said method further comprises:

comparing said measured value with the threshold value to determine whether the measured value deviates said predetermined amount from said threshold value.

12. A method according to claim 9, wherein said immiscible contaminant selected from the group consisting of: dirt, bone matter, skin, organ tissue, and immiscible soil.

13. A method according to claim 9, wherein said miscible contaminant selected from the group consisting of: blood, urine, and miscible soil.

14. A method according to claim 9, wherein said microbial decontamination process is selected from the group consisting of: a washing process, an antimicrobial treatment process and a rinsing process.

* * * * *